United States Patent [19]
Thal

[11] Patent Number: 6,024,758
[45] Date of Patent: *Feb. 15, 2000

[54] TWO-PART CAPTURED-LOOP KNOTLESS SUTURE ANCHOR ASSEMBLY

[76] Inventor: Raymond Thal, 11321 Bright Pond La., Reston, Va. 22094

[*] Notice: This patent is subject to a terminal disclaimer.

[21] Appl. No.: 09/027,741

[22] Filed: Feb. 23, 1998

[51] Int. Cl.$^7$ .................................................. A61B 17/00
[52] U.S. Cl. ............................................................ 606/232
[58] Field of Search ................................ 606/232, 73, 75; 24/706.2, 706.3, 711.4, 711.5, 360, 362, 356, 357, 358, 708, 707.9

[56] References Cited

U.S. PATENT DOCUMENTS

| | | |
|---|---|---|
| 4,007,743 | 2/1977 | Blake . |
| 4,532,926 | 8/1985 | O'Holla . |
| 4,632,101 | 12/1986 | Freedland . |
| 4,721,103 | 1/1988 | Freedland . |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. . |
| 5,192,203 | 3/1993 | Anzawa et al. . |
| 5,207,679 | 5/1993 | Li . |
| 5,224,946 | 7/1993 | Hayhurst et al. . |
| 5,236,445 | 8/1993 | Hayhurst et al. . |
| 5,370,662 | 12/1994 | Stone et al. . |
| 5,383,905 | 1/1995 | Golds et al. ............................. 606/232 |
| 5,569,306 | 10/1996 | Thal . |
| 5,658,313 | 8/1997 | Thal . |
| 5,665,112 | 9/1997 | Thal . |
| 5,683,419 | 11/1997 | Thal . |
| 5,709,708 | 1/1998 | Thal . |

*Primary Examiner*—Michael Buiz
*Assistant Examiner*—Vikki Trinh
*Attorney, Agent, or Firm*—Hoffman Wasson & Gitler PC

[57] ABSTRACT

A two-part captured-loop knotless suture anchor assembly which includes a suture anchor with a snag device thereon or therein, and a catch and loop device. The device facilitates reattachment and repair of soft tissue which has torn away from a bone mass.

10 Claims, 3 Drawing Sheets

TWO-PART CAPTURED-LOOP KNOTLESS SUTURE ANCHOR ASSEMBLY

BACKGROUND OF THE INVENTION

1. Field of the Invention

The present invention relates to an assembly used for tissue repair procedures. More particularly, there is provided a two-part captured-loop knotless suture anchor assembly that enables the attachment together or repair of biological tissue, such as tendons or ligaments on a bone surface.

2. Description of the Background Art

Soft tissues, such as tendons and ligaments, generally are attached to bone by small collagenous fibers. These connections are strong, but permit the tendons and ligaments to be flexible. When a soft tissue is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunneling techniques. These attachment devices are usually inserted through extensive surgical incisions, and, in some circumstances, by arthroscopic surgical techniques. The use of bone tunnels for repair can be difficult and generally require large open incisions. Recently, through endoscopic surgery, where the skilled surgeon looks into a joint cavity with a telescope, there has been a trend to repair soft tissues back to bone through small incisions called portals. Unique knotless suture anchor assemblies, such as depicted by the inventor in prior U.S. Pat. Nos. 5,569,306; 5,658,313; 5,665,112; 5,683,419; 5,709,708 and 5,720,765, the disclosure of which is incorporated by reference, have shown ways of facilitating this difficult and precise procedure.

A variety of devices are available for attaching objects to bone, such as screws, staples, cement, suture anchors, and sutures alone. These devices have been used to attach soft tissue, such as ligaments, tendons, muscles, as well as objects, such as prostheses, to bone. A suture anchor is a device which utilizes small anchors with suture materials usually attached thereto. A device, such as a screw, is inserted into the bone mass and anchored in place. After insertion of the anchor, the suture is passed through the soft tissue and tied into a know to secure the tissue to the bone The process of passing the anchor suture through the soft tissue and tying a knot is time consuming and difficult to undertake in the tight space encountered during endoscopic surgery and sometimes during conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926 can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946 and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

It is an object of the present invention to provide a two-part captured-loop knotless suture anchor assembly which is easy to use and install.

Another object of the present invention is to provide a suture anchor assembly which allows for secure attachment of soft tissue to a bone mass without the use or requirement of tying a knot.

Still another object of the present invention is to provide a suture anchor assembly which is compact and allows a surgeon to easily guide the anchor means into the bone mass, or an anchoring sleeve if desired, to enhance the security of the repair.

A primary feature of the present invention is a two-part, suture anchor and catch and loop device; knotless suture anchor assembly which is provided to draw a soft tissue to a bone mass.

SUMMARY OF THE INVENTION

In accordance with the above objects, the present invention is an enhanced two-part captured-loop knotless suture anchor assembly for attachment or reattachment of biological soft tissue to a bone mass. The unique two-part assembly includes a suture anchor having a snag device therein or thereon. A second integral component to the assembly is a catch and loop device. The catch loop device is made up of a suture loop and a catch device attached therewith. The suture loop is fed through the soft biological tissue so that the catch device which is attached to the suture loop is pulled taught and engages the tissue. The suture loop is then captured by a snag device, such as a recess, on the suture anchor. The anchor is then inserted into a bone mass drawing the soft tissue back into contact with the bone mass for repair. If desired, a hole can be predrilled in the bone mass for holding the suture anchor and/or a sleeve or collar can be inserted into the bone mass for securing and holding the anchor therein.

Incorporated by reference are U.S. Pat. Nos. 4,007,743; 4,632,101; 4,721,103; 4,870,957; 4,898,156; 4,946,468; 5,084,050; 5,102,421; 5,192,203 and 5,207,679 which all illustrate varying structures for the suture anchor.

The suture loop can be attached permanently to the catch device or can be attached in a hole therein or loop thereon.

Numerous other features of various embodiments of the two-part captured-loop knotless anchor assembly will be apparent from the following detailed description and the accompanying drawings.

DETAILED DESCRIPTION OF THE PREFERRED EMBODIMENT

Figure 1:
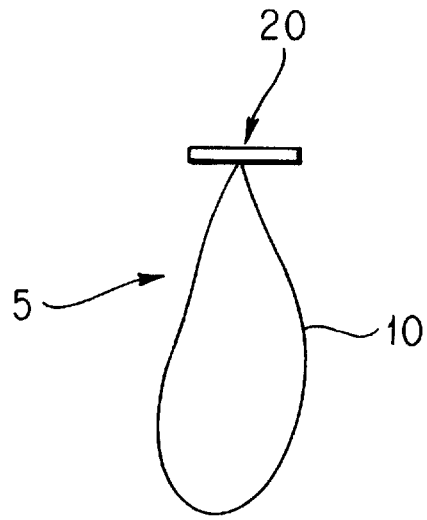
FIG. 1 is a perspective view of a catch and loop device component of the present invention.

FIG. 1 is a representative depiction of the catch and loop device 5 embodying an essential part of the invention. The suture loop 10 is a continuous loop of suture or a plurality of suture parts attached together and attached to a catch means 20. The suture loop 10 can be permanently attached to the catch device 20 or can be allowed to float through a tiny loop on the catch device 20.

The suture loop 10 can be made of any biodegradable or non-degradable suture material, as desired.

Figure 2:
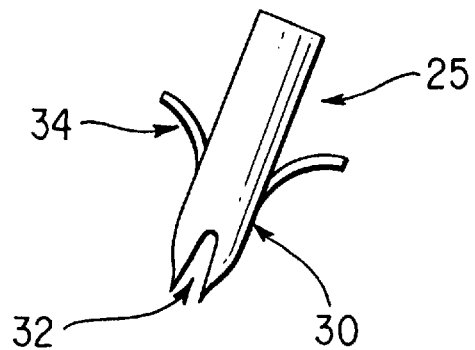
FIG. 2 is a perspective view of a suture anchor component of the present invention.

FIG. 2 depicts a suture anchor 25 suitable for the present invention. The anchor body 30 is provided with a snag means 32 depicted as a recess for engaging or grabbing a suture loop element 10 during a medical procedure. The snag means 32 can also be a hook, or like element, attached to the anchor body 30 for engaging or grabbing a suture loop element 10 during a procedure. The disclosure of U.S. Pat. No. 5,709,708, issued to the applicant, is incorporated by reference for the purpose of depicting various snag means configurations and suture anchor structures.

The depicted suture anchor 25 has at least one prong 34 for securely holding the anchor 25 to bone in a reattachment or attachment medical procedure.

Figure 3:
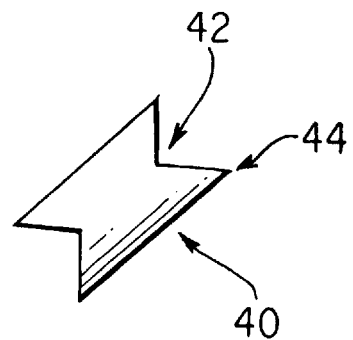
FIG. 3 is a perspective view of an alternate of a suture anchor component of the present invention.

FIG. 3 is a depiction of a suture anchor 40 especially suitable for combination with a plurality of catch and loop devices for ligament medical procedures. The suture anchor 40 is configured to have a snag means 42, depicted as a recess for engaging or grabbing the suture of a catch and loop device.

Additionally, the suture anchor 40 has a plurality of pointed edges 44 to grab bone during a medical procedure, such as ligament replacement or reattachment.

Figure 4:
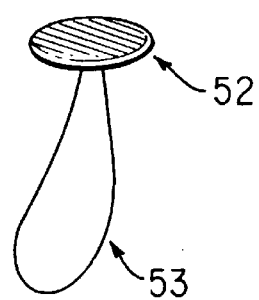
FIGS. 4 through 7 are perspective views of alternative embodiments of catch and loop devices of the present invention.
Figure 5:
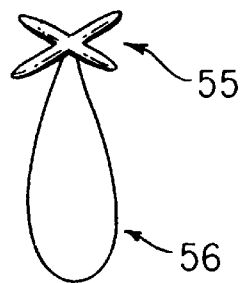

FIGS. 4 through 7, depict alternative structures for the catch device portion of the catch and loop device of the present invention. FIG. 4 depicts a button shaped catch device 52 which is attached to a suture loop 53. In FIG. 5, there is disclosed a cross-shaped catch device 55 which is attached to a suture loop 56.

Figure 6:
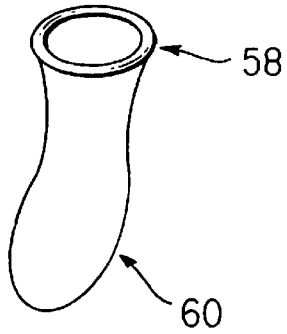
Figure 7:
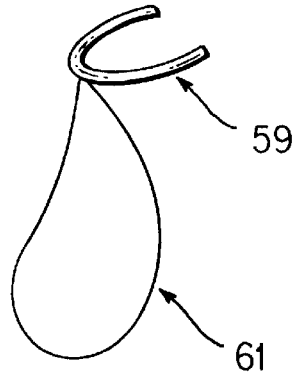

FIGS. 6 and 7, depict halo-shaped 58, and horseshoe-shaped 59 catch devices for use with suture loops 60 and 61, respectfully. Additional structures of the catch device are all contemplated to be part of the present invention and the structures depicted are illustrative and not for purpose of limitation.

Figure 8:
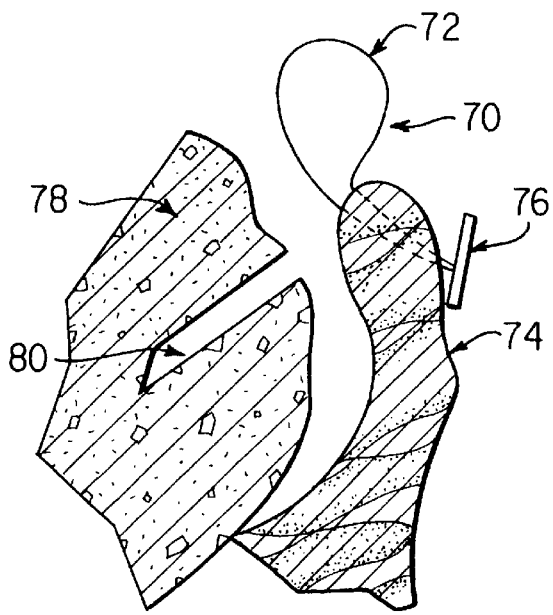
FIGS. 8 through 10 illustrate the procedure for attachment of a tissue to a bone mass for the embodiment outlines in FIGS. 1 and 2.
Figure 9:
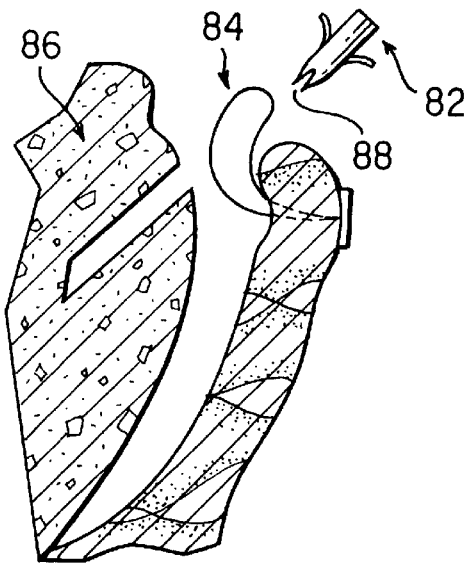
Figure 10:
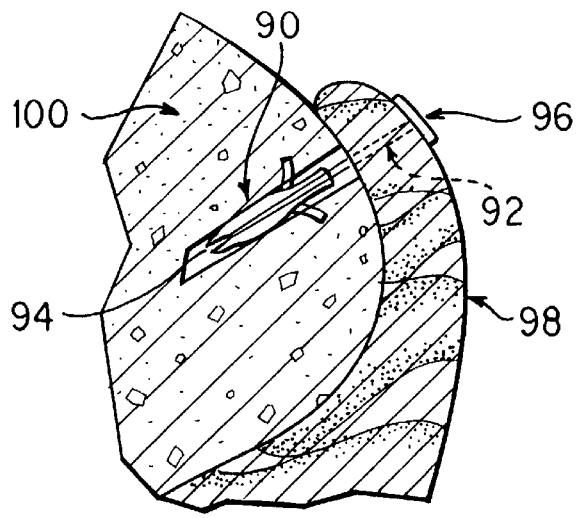

FIG. 8 through 10 depict step-wise a method for reattaching tissue to bone, using the two-part captured-loop knotless suture anchor assembly of the present invention.

In FIG. 8, a catch and loop device 70 has its suture loop 72 fed through tissue 74 so that the catch device 76 which is attached to the suture loop 72 is pulled taught and engages the tissue 74. The suture loop 72 is sized as desired for the particular patient or procedure. Bone mass 78 can be left as is or have a hole 80 predrilled therein. FIG. 9 illustrates a suture anchor 82, as was previously described in FIG. 2, which captures suture loop 84 in snag device 88 for engaging a bone mass 86.

FIG. 10 illustrates a completed repair using the two-part captured-loop knotless suture anchor assembly of the present invention. If desired, multiple two-part assemblies can be used for one repair. The suture anchor 90, pulls suture loop 92 taught by capturing same in snag device 94. The catch device 96 of the catch and loop device rests firmly on tissue 98 bring same into engagement with bone mass 100 for attachment and completion of the medical procedure.

Figure 11:
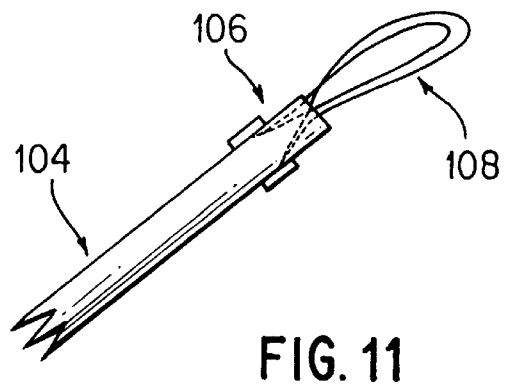
FIGS. 11 and 12 illustrate the procedure for attachment of a tissue to a bone mass for an alternative embodiment of the present invention.
Figure 12:
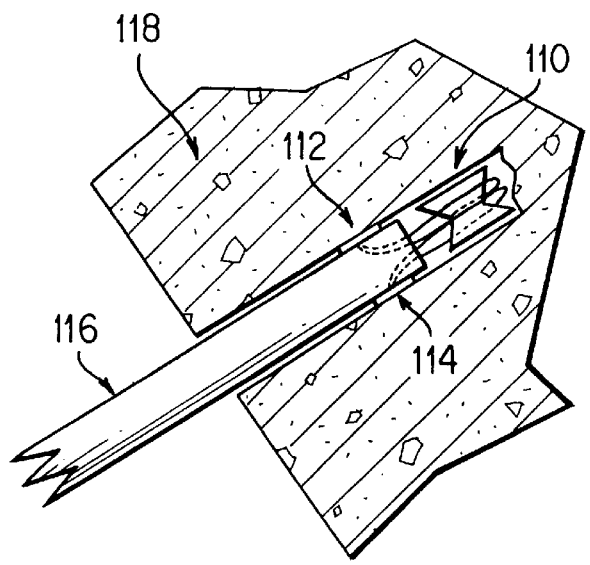

FIGS. 11 and 12 illustrate an alternate procedure for the two-part captured-loop knotless suture anchor assembly of the present invention. Procedures such as knee ligament repair or attachment are suitable for the novel assembly.

A ligament 104 is grabbed or caught by at least one catch and loop device 106. FIG. 11 depicts a ligament 104, being engaged or caught by two catch and loop devices 106 and 108, respectively.

A suture anchor 110 (FIG. 12) snags or engages the two loops of catch and suture devices 112 and 114, thereby securing the ligament 116 to the bone mass 118 effectuating a repair or reattachment of the ligament during, for example, an anterior cruciate ligament reattachment medical procedure.

In all embodiments, the suture anchor can be inserted into a sleeve which has first been inserted into the bone mass. The suture anchor is then securely held by the sleeve and further allows for ratcheting down by the suture anchor.

While a preferred and alternate embodiment of the invention are illustrated, it should be understood that the present disclosure is made by way of example and that variations to the structure shown and its use are possible within the scope of this disclosure without departing from the subject matter coming within the scope of the claims.

What is claimed is:

1. A two-part captured-loop knotless suture anchor assembly comprising:
   a suture anchor having a snag device; and
   at least one catch and loop device, whereby said snag device of said suture anchor engages said loop of said at least one catch and loop device to facilitate a repair or reattachment.

2. A two-part captured-loop knotless suture anchor assembly as claimed in claim 1, wherein said snag device is a notch or recess formed on a body of said suture anchor.

3. A two-part captured-loop knotless suture anchor assembly as claimed in claim 1, wherein said loop of said at least one catch and loop device is comprised of at least one suture element formed into a continuous loop and attached to at least one catch of said at least one catch and loop device.

4. A two-part captured-loop knotless suture anchor assembly as claimed in claim 1, wherein a catch of said catch and loop device is a disk, cross, bar, circle or horseshoe-shaped element.

5. A two-part captured-loop knotless suture anchor assembly as claimed in claim 1, wherein said suture anchor is an umbrella anchor or a wedge-type anchor.

6. A method for attachment of tissue to a bone mass utilizing said two-part captured-loop knotless suture anchor assembly as claimed in claim 1, comprising the steps of:
   a) passing said at least one loop device of said at least one catch and loop device through said tissue;

b) capturing said at least one loop device that has been passed through said tissue with said snag device; and c) installing said suture anchor into said bone mass.

7. A method for attachment of tissue to a bone mass utilizing said two-part captured-loop knotless suture anchor assembly as claimed in claim 6, further comprising the step of:

installing said suture anchor into a hollow anchoring sleeve which is installed into said bone mass.

8. A method for attaching a cruciate ligament graft to a bone mass utilizing said two-part captured-loop knotless suture anchor assembly as claimed in claim 1, comprising the steps of:

a) passing at least one loop of at least one catch and loop device through said cruciate ligament graft;

b) capturing said at least one loop of said at least one catch and loop device that has been passed through said cruciate ligament draft with said snag device; and c) installing said suture anchor into said bone mass.

9. A method for attachment of tissue to a bone mass utilizing said two-part captured-loop knotless suture anchor assembly as claimed in claim 8, further comprising the step of:

installing said suture anchor into a hollow anchoring sleeve which is installed into said bone mass.

10. A method for attachment of tissue to a bone mass utilizing said two-part captured-loop knotless suture anchor assembly as claimed in claim 8, wherein two catch and loop devices are utilized for a repair.

* * * * *